United States Patent [19]

Lopez

[11] Patent Number: 4,790,832
[45] Date of Patent: Dec. 13, 1988

[54] SYSTEM FOR ADMINISTERING MEDICATION NASALLY TO A PATIENT

[75] Inventor: George A. Lopez, Orange County, Calif.

[73] Assignee: ICU Medical, Inc., Mission Viejo, Calif.

[21] Appl. No.: 872,050

[22] Filed: Jun. 6, 1986

[51] Int. Cl.⁴ ............................................. A61M 25/00
[52] U.S. Cl. ..................................... 604/283; 604/83; 604/93
[58] Field of Search ..................................... 604/77, 93

[56] References Cited

U.S. PATENT DOCUMENTS

| | | | |
|---|---|---|---|
| 2,464,933 | 3/1949 | Kaslow | 604/270 |
| 3,276,472 | 10/1966 | Jinkens et al. | 604/83 |
| 4,390,017 | 6/1983 | Harrison et al. | 604/270 |

Primary Examiner—John D. Yasko
Attorney, Agent, or Firm—Whann & Connors

[57] ABSTRACT

Disclosed is a system for administering medication through the nasal passage of a patient into the patient's stomach. The system includes a connector having a body member with the passageway therein and extending between open ends in the body member. At each of these ends is a series of flanges with tapered edges. One of these ends is inserted into a tube extending through a patient's nose and into the patient's stomach. The other end is connected to either a suction or feeding pump at the appropriate time by a nurse. Within the body member is a port through which medication is introduced. A valve at the port either opens or closes the passageway as required.

3 Claims, 5 Drawing Sheets

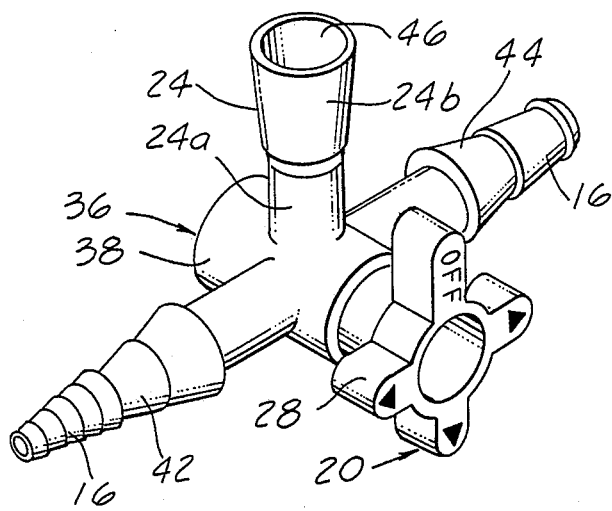
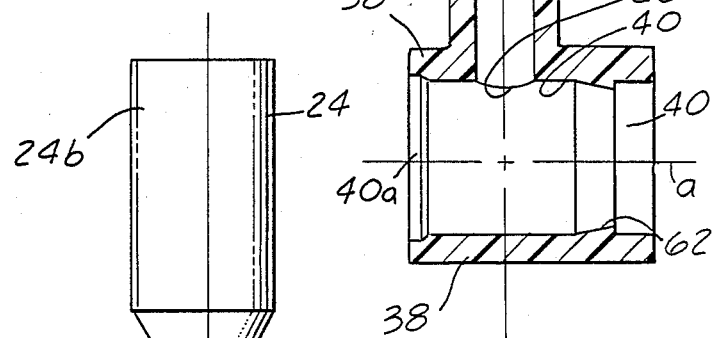
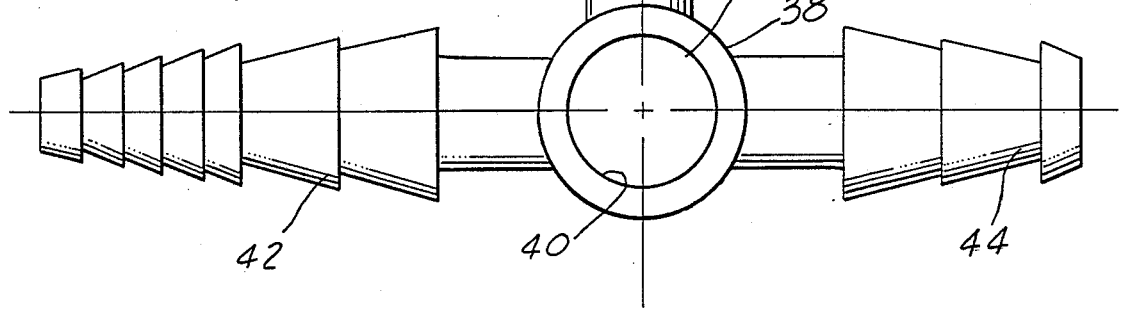
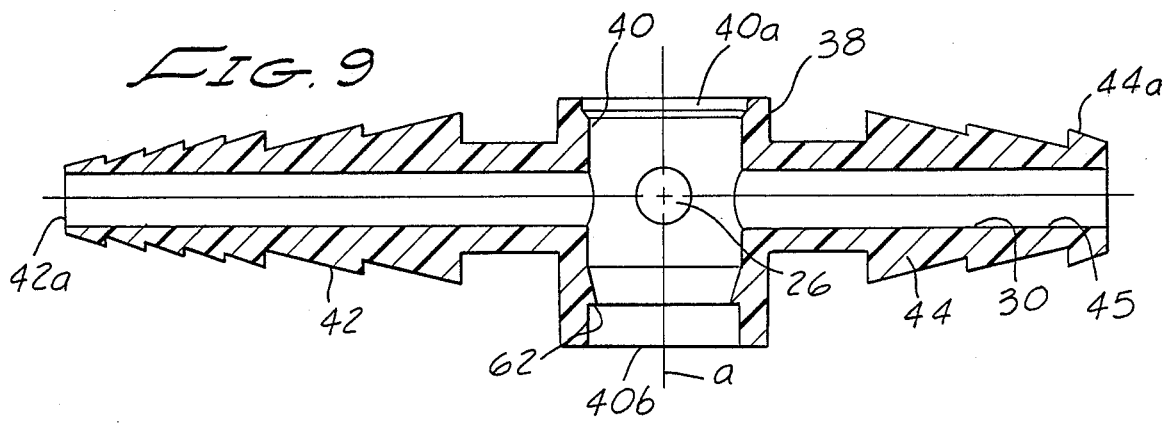

SYSTEM FOR ADMINISTERING MEDICATION NASALLY TO A PATIENT

BACKGROUND OF THE INVENTION

1. Field of the Invention

This invention relates to a system for administering medication through the nasal passage of a patient, particularly to a connector used in this system which includes a valve for opening and closing a passageway that introduces the medication through a tube that extends into the nose of the patient.

2. Background Discussion

In many instances a patient cannot receive medication and food through his mouth. In such cases, a nasal gastric tube is employed for introducing medication and food into the stomach of the patient and also for withdrawing fluid from the patient's stomach. This tube is a flexible plastic tube which comes in varying diamters depending upon the size of the patient and the nature of the medication being administered. This tube is fed through the patient's nose, down the esophagus into the patient's stomach. Care is taken not to insert the tube into the lungs of the patient. A portion of the tube extends from the one nostril of the patient and terminates at a point remote from a nostril. A plastic connector is inserted into this open end. This connector has a series of flanges of increasing diameter which will accommodate different sized tubes. There are two sets of flanges at each end of this connector, with the open ends of the connector being connected by a passageway. The end of the connector opposed to the nasal tube is connected to a second tube which is typically connected to a suction when it is desired to remove fluid from the patient's stomach, or to a feeding pump for pumping flood into the patient's stomach.

The current practice is to remove this connector from the tube coming from the patient's nose and then injecting medication into the tube. The nurse frequently is spattered with vomit or other fluid when he or she disconnects the connector. Also, occasionally the tube must be clamped off. This is done by removing the connector and attaching the clamp to the end of the tube coming from the patient's nose. This practice is not only a source of inconvenience and uncleanliness, but depending on the nature of the patient's illness, it may also be a way of communicating infectious diseases between the patient and the nurse. Spattering of the stomach fluid could contain infectious material that, if contacted with, for example, the eye of the nurse, could infect her with the disease of the patient.

MAJOR FEATURES OF THE INVENTION

The problems discussed above have been obviated by the present invention which provides a simple, convenient to use, and safe system for introducing food and medication into a patient nasally. There are several features of this invention, no single one of which is solely responsible for its desirable attributes. Without limiting the scope of this invention, as expressed by the claims, its more prominent features will now be discussed briefly. After considering this discussion, and particularly after reading the section of this application entitled Detailed Description of the Preferred Embodiments, one will understand how the features of this invention provide the advantages of simplicity, convenience and safety.

One feature of this invention is the employment of a connector which includes a port that allows medication to be introduced into and through the connector and then through the tube extending into the patient's nose. This port is opened and closed by a valve which is manually manipulated. Thus, the connector used in the system of this invention need not be removed, and is not removed, to administer medication to the patient.

Another feature of this invention is that one end of the connector has an internal taper that allows the tapered end of the feeding tube coming from the feeding pump to be inserted into and held securely in the connector. In other words, the connector includes a female type receptical that mates with the tapered male end of the feeding tube.

A third feature of this invention is that the port is surrounded by a funnel which has a barrel that is tapered inwardly to receive the tapered end of a gastric syringe. This syringe is inserted into the open end of the barrel and fits snugly into the tapered section of the barrel.

A fourth feature of this invention is that the connector employs a stop-cock type valve which is moveable to a plurality of different positions. In one position, the port is opened but through the connector the passageway is blocked to prevent food from being pumped into the tube. The open port, however, allows medication to be fed through the port, connector, and tube, into the patient. In the second position it is moved to block the port so that medication cannot be fed into the connector but opens the passageway through the connector to allow either food to be pumped into the patient or fluid to be pumped from the patient's stomach.

The preferred embodiments of the invention illustrating all its features will not be discussed in detail. These embodiments show the connector of this invention being connected to two tubes, one of which is inserted through the patient's nose into the patient's stomach, allowing medication to be administered to the patient without detaching the connector from the tubes.

BRIEF DESCRIPTION OF THE DRAWING

The system of this invention is illustrated in the drawing, with like numerals indicating like parts, in which

FIG. 7 is a perspective view of a second embodiment of the connector of this invention.

FIG. 8 is a side elevational view of the body of the connector shown in FIG. 7 with the valve removed.

FIG. 9 is a cross-sectional view taken along line 9—9 of FIG. 8.

FIG. 10 is a cross-sectional view taken along line 10—10 of FIG. 8.

DESCRIPTION OF THE PREFERRED EMBODIMENTS

Figure 1:
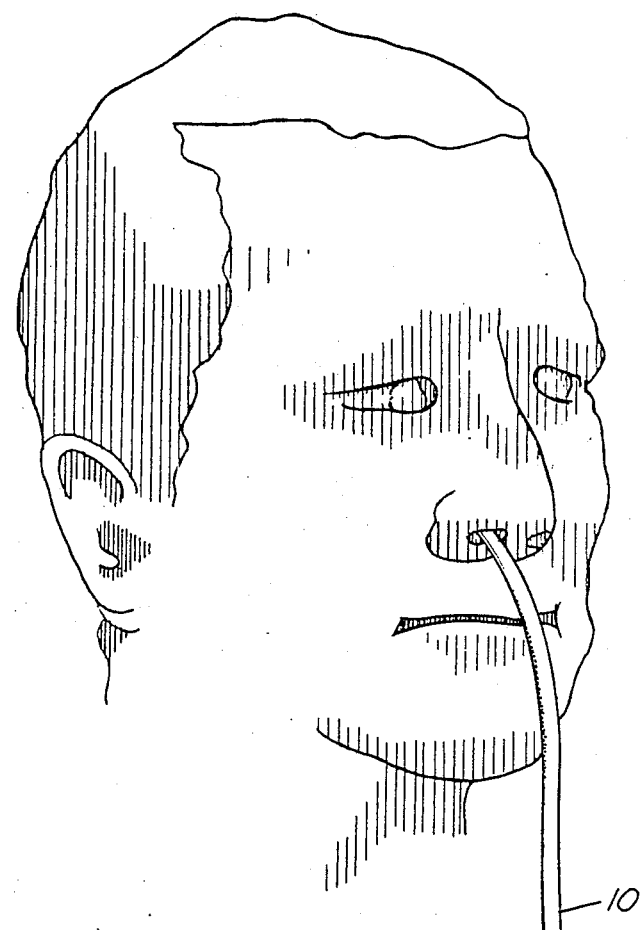
FIG. 1 is a schematic drawing illustrating the conventional system for administering medication nasally to a patient.
Figure 2:
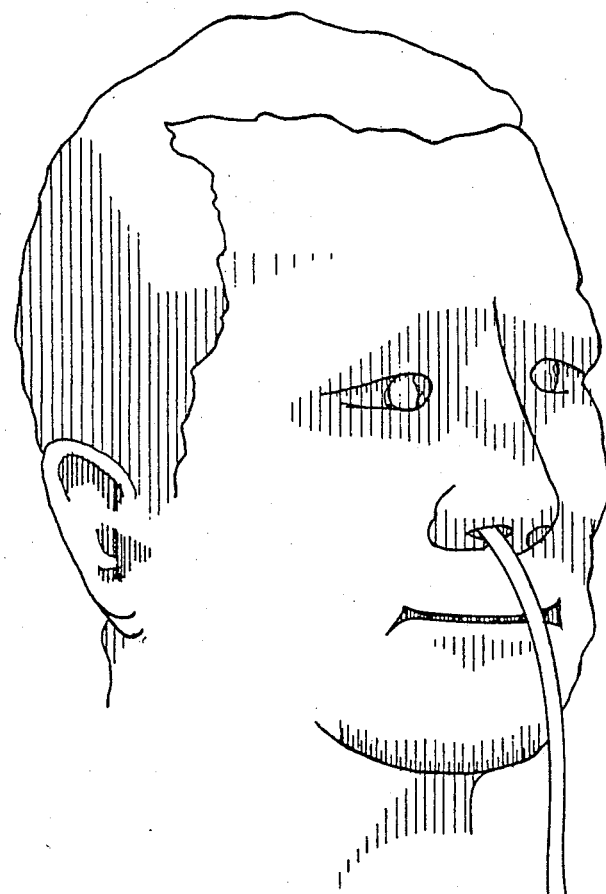
FIG. 2 is a schematic drawing illustrating the system of the present invention.

FIG. 1 illustrates the conventional practice for adminiserting food and medication nasally to a patient. A flexible tube 10 is inserted into the patient's nose and fed through his esophagus down into his stomach, care being taken not to insert the tube into the patient's lungs. To the end of the tube extending from the patient's nose is inserted a conventional connector 12. This conventional connector 12 includes a body member 14 having a passageway (not shown) extending from one open end of the connector to the other open end of the connector and on the outside of the body member at the ends, a series of flanges 16. The flange nearest an end has the smallest diameter, with the flange most remote from an end having the largest diameter. The flanges in between the ends increase in diameter incrementally. One end of the connector 12 is inserted into the open end of the tube 10 extending from the patient's nose and the other end of the connector is inserted into the open end of another tube 18 leading to either a suction pump for withdrawing fluid from the patient or a feeding pump which pumps food into the patient.

When the nurse desires to introduce medication through the tube 10 into the patient's stomach, she pulls the one end of the connector from the tube 10 and then injects the medication through the open end of the tube using, for example, a syringe. This practice is both inconvenient, messy, and dangerous. Frequently, the tube includes vomit or other fluids that are spattered over the nurse when she removes the connector 12. If this vomit carries infectious bacteria and it is splattered into her eye, for example, the nurse could become infected. Further, the vomit and other body fluids are often splashed on the patient's bedding and clothing of the nurse which requires a change of bedding and clothes.

Figure 5:
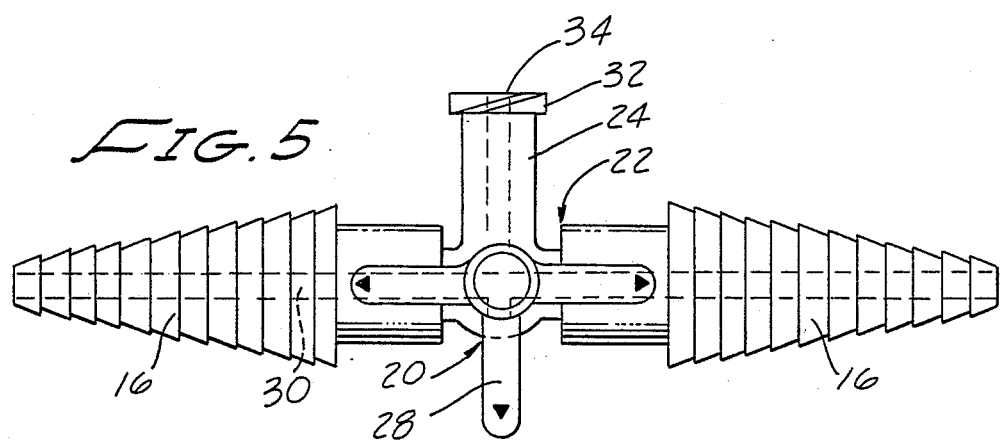
FIG. 5 is a side elevational view of one embodiment of the connector of this invention with the valve in a third position.
Figure 6:
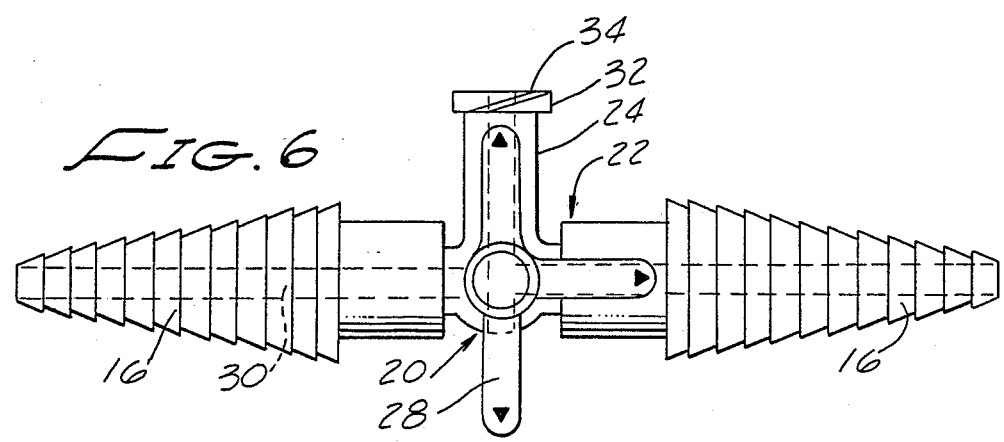
FIG. 6 is a side elevational view of one embodiment of the connector of this invention with the valve in a fourth position.

In accordance with this invention, the connector 12 has been modified by including in its structure a valve 20 that allows medication to be introduced into the tube 10 without removal of the connector 12. The connector 22 of this invention includes a funnel 24 which leads to a port 26 (FIG. 9) that is open or closed depending upon the position of the valve 20. The valve 20 has a handle 28 which is manually manipulated by the nurse and is moveable to four different positions as illustrated respectively in FIGS. 3 through 6. In the first position shown in FIG. 3, the port is open as well a passageway 30 extending between both ends of the connector 22. This position would be utilized when it is desired to draw suction to clear both the passageway 30 and the funnel 24. The valve position shown in FIG. 4 closes off one of the passageway 30 allowing medication to be fed through the funnel 24 and the left hand half of the passageway, as viewed in FIG. 4 through the open end and tube 10 into the patient. In FIG. 5 the valve has been moved to a position where the port 26 is closed off but the passageway 30 is open to allow either food to be pumped into the patient or suction to be applied to remove fluid from the patient. FIG. 6 illustrates the valve position where the port 26 is open and the right hand side of the passageway is open but the left hand passageway is closed as viewed in this FIG. 6. This position would be used to draw suction, for example, to clear the funnel 24 but not pull any suction through the tube 10 to remove fluid from the patient's stomach. The embodiment of the connector illustrated in FIGS. 3 through 6 has at the entry end of the funnel a lip 32 with a slanted groove 34 therein which provides a lurelock connection. In this embodiment, medication can be introduced using a tight fitting lure lock on the syringe that would screw on to the entry end of the funnel 24.

The second embodiment of the connector of this invention is shown in FIGS. 7 through 13. This connector 36 includes a body member 38 having a cylindrical chamber 40 centrally located which receives the valve 20. This chamber 40 has two open ends, 40a and 40b. At right angles to the longitudinal axis a of the chamber 40 are two outwardly extending rigid tubes 42 and 44 having flanges 16 along their exteriors. The one tube 42 has a series of seven flanges, the other tube 44 has a series of three flanges. The tube 42 best suited for insertion in the end of the tube 10 extending from the patient. The other tube 44 is best adapted to fix into the tube 18. As best shown in FIG. 9, the passageway segment extending from the chamber 40 to the end 42a has a diameter of 0.15 inches. The passageway segment extending from the chamber 40 to the other end 44a has an outwardly tapered end portion 45. The diameter of this passageway adjacent to taper is 0.145 inches and approximately three quarters down the length of this passageway it begins to expand outwardly to terminate in the diameter of 0.170 inch.

The chamber 40 has on its exterior the port 26 which allows medication to be introduced into the passageway 30. The diameter of this port is approximately equal to the diameter of the passageway 30 or is about 0.145 inch. It is desirable to have this port as large as possible in order to accommodate powdery type medication such as, for example, pulverized aspirin. Surrounding this port 26 is the funnel 24 which includes a neck section 24a and a barrel section 24b with the entry into the funnel being designed to accommodate the tip of a gastric syringe. This barrel section 24b thus has an inwardly tapering sidewall 46 which matches the taper of the injection tip of the syringe to allow the syringe to be fitted snugly within the barrel section 24b. The barrel section 24b terminates in an opening which leads to a passageway 48 extending through the neck section 24a to the port 26.

Figure 11:
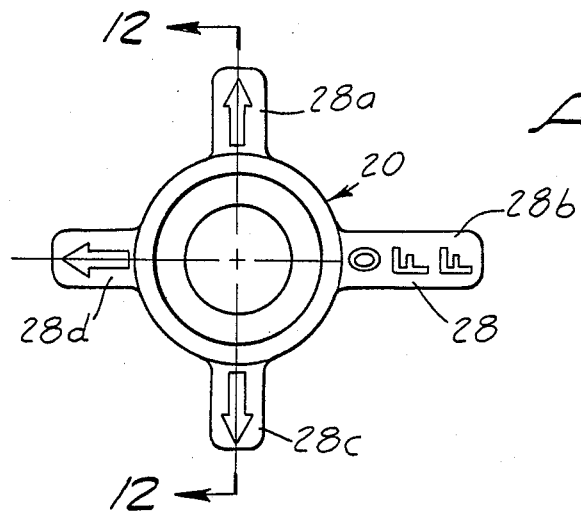
FIG. 11 is a plan view of the valve used in the connector shown in FIG. 7.
Figure 12:
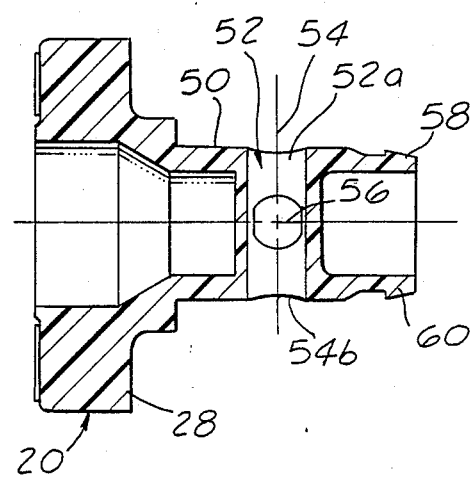
FIG. 12 is a cross-sectional view taken along line 12—12 of FIG. 11.
Figure 13:
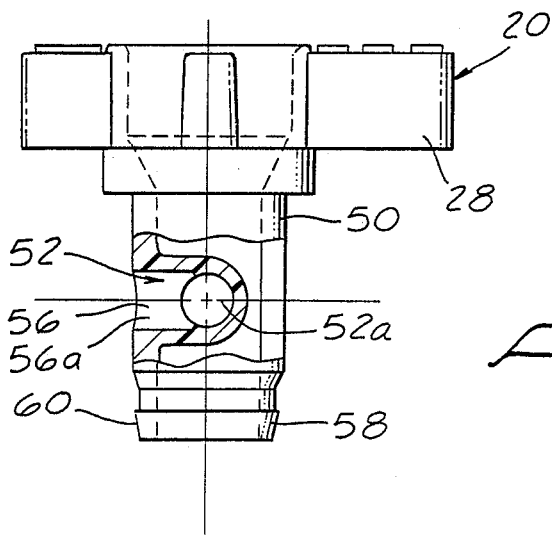
FIG. 13 is a side elevational view with sections broken away of the valve shown in FIG. 11.

The valve is illustrated in FIGS. 11 through 13, and it includes a cylindrical body section 50 which fits into the chamber 40. The valve 20 includes a T-shaped channel 52. This channel 52 consists of one leg 52a that has two open ends 54a and 54b. Extending at a right angle from this leg 52a is a second leg 56 which, when properly aligned, will have its open end 56a be in registration with the port 26. By turning the valve 20 into the different positions, as illustrated in FIGS. 3 through 6, the valve will either open or close the passageway 30 leading to the patient or open and close the port 26 for introducing medication through this passageway into the patient. The handle 28 of the valve is integral with the valve body 38 and includes four fingers 38a-d with arrows on three of the fingers to indicate the valve position. The longest finger 28b has the word "off" on it. The "off" position corresponds to the position where the legs 52a and 56 intersect, and is opposite the leg 56.

The valve is inserted into the valve chamber 40 so that the end 58 will extend out the one open side of the chamber. There is a tapered lip 50 in this end which snaps into locking engagement with a shoulder 62 in the chamber 40 to secure the valve 20 in position. Preferably a lubricant is applied to the exterior of the valve body 38 prior to insertion into the valve chamber 40. The body of the connector is molded from a plastic which has been approved by the FDA for medical purposes, the valve is molded from a different plastic, which has also been approved for medical uses.

OPERATION

To use this invention, the nurse simply inserts the one end of the connector 36 into the open end of the tube 10 extending from the patient's nose and moves the valve 20 to the position shown in FIG. 6. With the valve 20 in this position, no foreign or unwanted materials will enter into the tube through the connector. In effect, the tube 10 has been closed off with the valve in this position.

If the nurse desires to apply suction to remove stomach fluids from the patient, the second tube 18 is attached to the connector 36 at the end 44a by inserting this end into the open end of the suction tube. The valve 20 is then moved to the position shown in FIG. 5. Suction is then drawn, with the passageway 30 being open and the leg of the T-channel being aligned so that the ends 54a and 54b of this leg 52a are in registration with the ends 42a and 44a of the passageway 30. The port 26 is closed off at this time so that fluids will not escape through the port and out the funnel 24. Thus fluid flows directly from one end of the connector to the other to a sump (not shown).

If it is desired to feed food to the patient, the valve is maintained in the position shown in FIG. 5 and the end of the tube through which the food flows is inserted into the end 44a of the passageway 30. The feeding tube will normally have a tapered end which will fit in a mating relationship snugly into the tapered end 44a of the passageway. The fit will be tight so that the feeding tube cannot be readily removed unless force is applied to pull the feeding tube from the tapered end 44a of the passageway 30.

Figure 4:
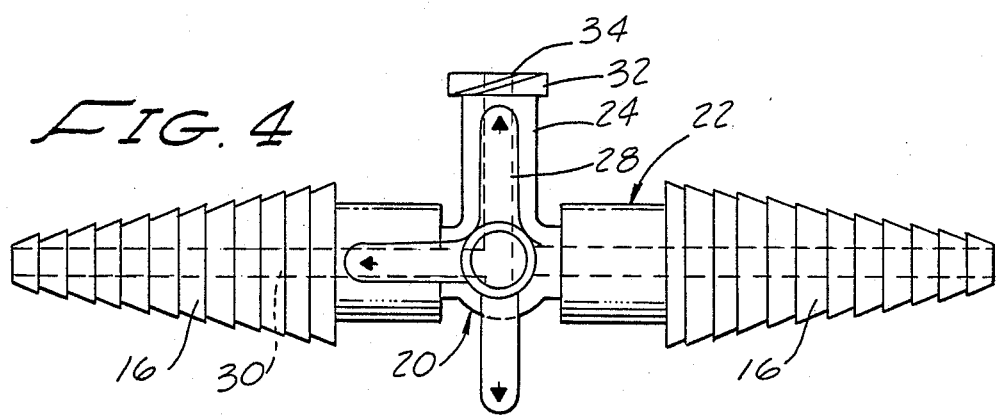
FIG. 4 is a side elevational view of one embodiment of the connector of this invention with the valve in a second position.

When medication is to be administered to the patient, the valve 20 is moved to the position illustrated in FIG. 4. In this position the leg 52a is aligned so that the one end 54a of the leg is opposite the port 26 and the one end 56a of the leg 56 is opposite the end 42a of the passageway 30. The nurse then will insert the end of the syringe into the tapered end of the barrel 24b and inject the medication through the funnel 24. The medication will flow through the passageway 48 in the neck 24a of the funnel 24 through the leg 52 and the leg 56 into the passageway 30 and through the tube 10 into the patient's stomach. Since the port 26 and passageway 30 are relatively large in diameter, if the medication is a granular or powder material, it will not likely clog the port. If it does, however, the valve can be moved to the position shown in FIG. 6 and suction applied to clear the port.

Figure 3:
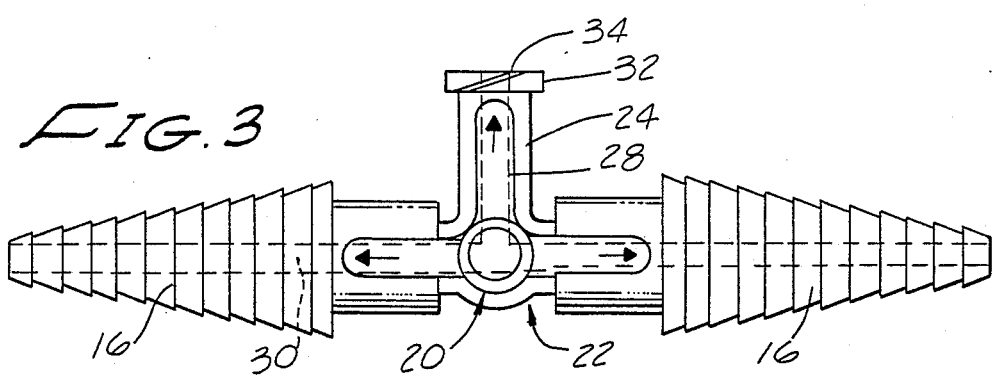
FIG. 3 is a side elevational view of one embodiment of the connector of this invention with the valve in its first position.

If it is desired to allow the passageways 48 and 30 to be opened to the atmosphere, the valve is moved to the position illustrated in FIG. 3. Here the T-channel will be aligned so that the end 56a of the leg 56 is opposite the port 26 and the ends 54 and 54b of the leg 52a are, respectively, aligned with ends 42a and 44a of the passageway 30.

SCOPE OF THE INVENTION

The above description presents the best mode contemplated of carrying out the present invention. This invention is, however, susceptible to modifications and alternate constructions from the embodiments shown in the drawing and described above. Consequently, it is not the intention to limit this invention to the particular embodiments disclosed. On the contrary, the intention is to cover all modifications and alternate constructions within the spirit and scope of the invention as expressed by the claims.

What is claimed is:

1. A system including
   means for introducing, food into the stomach of a patient or removing fluid from the stomach through tubular means extending through the nose of the patient into the stomach of the patient, and for periodically introducing medication into the stomach through the tubular means, said tubular means varying in diameter for different patients,
   said tubular means including
   first tubular means having a first open end adapted to extend through the patient's nose and into the patient's stomach and a second end terminating at a point remote from the nose and removably attached to a connector,
   said connector comprising a body member having opposed first and second ends and a passageway extending through the body member between said first and second ends thereof, said body member having at said first and second ends a series of flanges having tapered edges so that each of said ends of the body member may be inserted into the open end of one of several different tubes varying in diameter, said first end of the body member being inserted into the second open end of the first tubular means, and a port between the open ends of the body member which is in communication with the passageway, a funnel member at the port which is adapted to receive the delivery end of a gastric syringe, and valve means including a cavity and a valve body member having therein a T-shaped channel, said valve body member being rotatably received in the cavity so that the T-shaped channel is in alignment with the passageway and the port to enable the port to be opened or closed, or the passageway to be opened or closed, in accordance with the position of the valve body member in the cavity, and
   second tubular means having one end thereof connected to the second open of the body member and another end connected to means for pumping food into the stomach of the patient through the second tubular means, connector, and first tubular means or removing fluid from the stomach of the patient through the first tubular means, connector, and second tubular means.

2. The system of claim 1 wherein the funnel member has inwardly tapered barrel that is adapted to receive a tapered end of the gastric syringe.

3. The system of claim 1 wherein the end of the passageway extending into the second tubular means has a inwardly tapered end section and the tubular means has a corresponding tapered end which fits into the tapered end of the passageway.

* * * * *